United States Patent [19]

Yamada et al.

[11] 4,389,346

[45] Jun. 21, 1983

[54] ESTERIFICATION REACTION PRODUCTS AND COSMETICS CONTAINING SAME

[75] Inventors: Osamu Yamada, Yokohama; Yuzo Higaki, Machida; Akitoshi Ukai, Yokohama, all of Japan

[73] Assignee: The Nisshin Oil Mills, Limited, Tokyo, Japan

[21] Appl. No.: 235,405

[22] Filed: Feb. 18, 1981

[30] Foreign Application Priority Data

Feb. 18, 1980 [JP] Japan ................................. 55-17761

[51] Int. Cl.³ ............................................. C11C 3/02
[52] U.S. Cl. .................. 260/410.7; 260/104; 424/63; 424/64; 424/69; 424/70
[58] Field of Search ................... 260/104, 410.7, 410.6; 424/63, 64, 69, 70

[56] References Cited

U.S. PATENT DOCUMENTS

| | | | |
|---|---|---|---|
| 1,937,533 | 12/1933 | Rosenblum | 260/104 |
| 2,294,229 | 8/1942 | Fiero | 424/64 |
| 2,950,313 | 8/1960 | Kirkpatrick | 260/104 |
| 3,088,876 | 5/1963 | Buth | 424/64 |
| 3,642,980 | 2/1972 | Lachampt et al. | 424/64 |

*Primary Examiner*—John F. Niebling
*Attorney, Agent, or Firm*—Sughrue, Mion, Zinn, Macpeak & Seas

[57] ABSTRACT

There are provided esterification reaction products between a condensate of polyhydric alcohol having 2–4 hydroxyl groups and an acid mixture comprising 12-hydroxy stearic acid and resin acid, the molecule of which has hydroxyl groups of not more than half relative to the total hydroxyl groups of said condensate of polyhydric alcohol. These esterification products are a semitransparent, paste-like substance with a light yellow and suitable properties for use in the basic material for cosmetics.

4 Claims, No Drawings

ESTERIFICATION REACTION PRODUCTS AND COSMETICS CONTAINING SAME

BACKGROUND OF THE INVENTION

This invention relates to a new, paste-like esterification reaction product and cosmetics containing same.

The inventors found before that esterification reaction products between a condensate of polyhydric alcohol of 2-4 hydroxyl groups and 12-hydroxy stearic acid exhibit a good consistency, hydrating property, self-emulsifying property and miscibility with cosmetic materials and have flexibility without rendering the greasy touch to the skin, which are a wax-like substance with uniform composition and improved qualities and therefore, are useful in use for the basic material of cosmetics (Japanese Patent Kokai No. 54-109917). However, these esterification products are not sufficiently satisfied in transparency, glossiness and temperature-stability as the basic material for cosmetics.

SUMMARY OF THE INVENTION

An object of this invention is to provide a paste-like substance improved in glossiness, transparency, temperature-stability and pigment-dispersibility and exhibiting a good consistency, hydrating property, self-emulsifying property, miscibility with cosmetic ingredients, flexibility and stable qualities.

In accordance with this invention, there are provided esterification reaction products between a condensate of polyhydric alcohol having 2-4 hydroxyl groups, represented by the general formula, $$(HO)_nR-O-R(OH)_n$$

wherein Rs both are a moiety having removed hydroxyl groups from polyhydric alcohol of 2-4 hydroxyl groups and ns both are 1, 2 or 3 and an acid mixture comprising 12-hydroxy stearic acid and resin acid containing the resin acid content of not more than 50 mol %, the molecule of which has not more than half the hydroxyl groups relative to the total hydroxyl groups of said condensate of polyhydric alcohol.

DETAILED DESCRIPTION OF THE INVENTION

The condensates of polyhydric alcohol represented by the general formula are, for example, dipropylene glycol, diglycerine, dipentaerythritol and ditrimethylolpropane. These compounds are well-known and may be prepared by conventional methods.

The resin acid which may be used is, for example, abietic acid, dehydroabietic acid, neoabietic acid, palustric acid, pimaric acid, iso-pimaric acid and rhodinic acid. Also, the resin acid may be in part substituted by a straight chain fatty acid of 10 or more carbon atoms and/or a branched chain fatty acid of 8 or more carbon atoms, if necessary.

The straight chain fatty acid of 10 or more carbon atoms may be represented by the formula, $$R_1COOH$$

wherein $R_1$ is an alkyl group of 9 or more carbon atoms, and for example, decanoic acid, lauric acid, myristic acid, palmitic acid, stearic acid and behenic acid.

As to the branched chain fatty acid or 8 or more carbon atoms, it is difficult to mention the general formula to embrace all the corresponding compounds, though there are exemplified 2-ethylhexanoic acid, 3,5,5-trimethylhexanoic acid, tetramethylnonanoic acid of the formula, $$CH_3-(CH_2)_n-CH_2-COOH$$
$$|$$
$$(CH_3)_m$$

wherein m is 3-4 and n is 6-7, 2-hexyldecanoic acid, 2-heptylundecanoic acid and isostearic acid.

The esterification reaction products of this invention are a light yellow, semitransparent, paste-like substance and their properties such as melting point, degree of consistency and hydrating property can be adjusted by varying a type of the starting fatty acid and resin and a degree of esterification bond. The foregoing is one of the characteristics of this invention similarly to the invention of Japanese Patent Kokai No. 54-109917.

Particularly, according to this invention, the esterification products are remarkably improved in glossiness, temperature-stability, transparency and pigment-dispersibility and also, these properties can be adjusted properly.

The amount of resin acid to be used is not more than 50 mol % based on the total of 12-hydroxystearic acid (hereinafter referred to as 12-OHst) and resin acid. If the amount exceeds 50 mol %, the resulting esterification products have a lower melting point and do not exhibit a paste-like form at normal temperature and further, the colour, touch and pigment-dispersibility are remarkably reduced so that the desired properties intended in this invention can not be obtained. Though the upper limit of the amount of resin acid is not particularly defined, 1 mol % is preferred.

If necessary in this invention, a part of the resin acid which is one of the above-mentioned acid components may be substituted by a straight chain fatty acid of 10 or more carbon atoms and/or a branched chain fatty acid of 8 or more carbon atoms. However, if the total of these fatty acid and resin acid exceeds 50 mol % of the total of the acid components including 12-OHst, the resulting esterification products do not have the desired properties of this invention in respect of the hydrating property, consistency and touch. If a straight chain fatty acid of 9 or less carbon atoms or a branched chain fatty acid of 7 or less carbon atoms are used, the esterification product has an undesired odour and irritant effect on the skin.

The ratio of the resin acid to the straight chain and/or branched chain fatty acid is not particularly limited, though the resin acid is within the range of preferably, 10-50 mol % based on the total of both.

The esterification reaction may be carried out by conventional methods in the presence of or in the absence of a catalyst. Examples of the catalyst, if used, include an acid catalyst such as sulfuric acid and p-toluene-sulfonic acid; a metal oxide such as tin oxide and zinc oxide and a metal chloride such as tin chloride and zinc chloride. The reaction of polyhydric alcohol condensates with acid components including 12-OHst is advanced to be not more than half the remaining OH group number in one molecule of the resulting product relative to the total number of OH groups in the starting polyhydric alcohol condensate. By way of example, the reaction amount of the acid components to 1.0 mol of the various polyhydric alcohol condensates is calculated as follows:

4 mols rhodinic acid is added as a comparative example (Sample No. 8).

TABLE 1

| | | Dipropylene glycol | Diglycerine | Ditrimethylol-propane | Dipentaerythritol |
|---|---|---|---|---|---|
| (1) | Polyhydric alcohol condensates | | | | |
| (2) | Reaction amount of (1) | 1 mol | 1 mol | 1 mol | 1 mol |
| (3) | Reaction amount of total acid components including 12-OHst | 1~2 mols | 2~4 mols | 2~4 mols | 3~6 mols |
| | Details of (3) | | | | |
| (4) | Reaction amount of 12-OHst [50~100 mol % of (3)] | 0.5~2 mols | 1~4 mols | 1~4 mols | 1.5~6 mols |
| (5) | Reaction amount of rhodinic acid [1~50 mol % of (3)] | 0.01~1 mol | 0.02~2 mols | 0.02~2 mols | 0.03~3 mols |
| (6) | Reaction amount of n-$C_{10}$~FA and/or iso-$C_8$~FA [50~90 mol % of (5)] | 0.005~0.9 mols | 0.01~1.8 mols | 0.01~1.8 mols | 0.015~2.7 mols |

TABLE 2

| Sample No. | Esterification Products | Color | Odor | Number of OH groups *5 | MP (°C.) | Consistency at 25° C. *6 | Hydrating Ability *7 (g) | Transparency *8 (cm) | Glossiness *9 |
|---|---|---|---|---|---|---|---|---|---|
| 1 | Est. Product of 1 mol diglycerine, 2 mol 12-OHst and 1 mol rhodinic acid *1 | Light yellow | None | 1 | 23~27 | 235 | 13.0 | >30 | A |
| 2 | Est. Product of 1 mol dipentaerythritol, 4 mols 12-OHst and 1 mol rhodinic acid *2 | Light yellow | " | 1 | 25~29 | 120 | 11.0 | >30 | A |
| 3 | Est. Product of 1 mol dipentaerythritol, 4 mols 12-OHst, 1.5 mols stearic acid and 0.5 mols rhodinic acid *3 | Light yellow | " | 0 | 27~31 | 105 | 12.0 | >30 | A |
| 4 | Petrolatum | Light yellow~white | Little | — | 38~60 | 79 | 1.7 | 3 | D |
| 5 | Hydrogenated castor oil | White | " | — | 85~88 | 0 | 0 | 0 | C |
| 6 | Lanolin | Yellow | Offensive | — | 34~38 | 115 | 14.5 | 1 | C |
| 7 | Dipentaerythritol-hexa 12-OHst ester | White | None | 0 | 37~47 | 40 | 10.5 | 15 | B |
| 8 | Est. Product of 1 mol dipentaerythritol, 2 mols 12-OHst and 4 mols rhodinic acid *4 | Red-brown | None | 0 | <10 | >300 | 3.5 | >30 | A |

Notes
*1: The main component is diglycerinemonorhodinic acid di-12-OHst ester.
*2: The main component is dipentaerythritolmonorhodinic acid tetra-12-OHst ester.
*3: The main component is dipentaerythritolhemirhodinic acid sesquistearic acid tetra-12-OHst ester.
*4: The main component is dipentaerythritoltetrarhodinic acid di-12-OHst ester.
*5: Number of the remaining OH groups which originate from the starting polyhydric alcohol condensate.
*6: Measured in accordance with the method of JIS K 2560 using a cone of synthetic resin as prescribed in JIS K 2809, consistency testers for grease and petrolatum.
*7: Indicated in increased amount of water at 25° C. by adding distilled water to 10 g of a sample while stirring sufficiently, further impregnating with an excess of distilled water, allowing to stand for three days and thereafter removing the excess water by drying.
*8: Indicated in a distance such that a letter on a white paper (an alphabet letter of 2 cm square in size: A) can be read through a sample of 0.3 cm in thickness.
*9: Rated in appearance as follows: A: Glossiest, B: Glossy, C: Somewhat glossy, D: Non glossy Amounts of the components may be decided properly from the ranges set forth in Table 1 to conduct the esterification reaction.

After completion of the esterification the reaction product mixture is subjected to a deacidification, decoloration and deodorization treatment, if necessary. The obtained products are a light-colored, odorless, paste-like substance.

Physical properties of esterification products of this invention are set forth in Table 2 together with, for the purpose of comparison, petrolatum, hydrogenated castor oil, lanolin and an esterification product of Japanese Patent Kokai No. 54-109917 (Dipentaerythritolhexa 12-OHst ester). Also, an esterification product using resin acid of more than 50 mol % based on the total of the resin acid and 12-OHst, namely the esterification product of 1 mol dipentaerythritol, 2 mols 12-OHst and The products of Sample Nos. 1-3 were synthesized by the methods of Examples 1 and 2 and in accordance with these methods.

As is apparent from the above Table, the esterification products of this invention are in form of a smooth paste at room temperature (25° C.) having a good hydrating ability which brings about a self-emulsifying property. Also, they are superior in a transparency and glossiness to esterification products of Japanese Patent Kokai No. 54-109917 and have properties suitable for use as a cosmetic basic material. In case of incorporating a resin acid of more than 50 mol % (Sample No. 8), the resulting product is reduced in melting point, red-brown coloured and inferior in the hydrating ability.

Next, in order to review a temperature-stability of these esterification products, a consistency changing rate was determined by measuring consistency at indicated temperatures. The samples set forth in Table 2 were used for the test.

TABLE 3

| Sample No. | Consistency 5° C. | 15° C. | 25° C. | 35° C. | Consistency Changing Rate(*) 5~15° C. | 15~25° C. | 25~35° C. | 5~35° C. |
|---|---|---|---|---|---|---|---|---|
| 1 | 124 | 190 | 235 | >300 | 0.53 | 0.24 | — | — |
| 2 | 55 | 82 | 120 | 243 | 0.49 | 0.46 | 1.03 | 3.42 |
| 3 | 41 | 78 | 105 | 200 | 0.90 | 0.35 | 0.90 | 3.88 |
| 4 | 31 | 50 | 79 | 120 | 0.61 | 0.58 | 0.52 | 2.87 |
| 5 | 0 | 0 | 0 | 0 | — | — | — | — |
| 6 | 0 | 56 | 115 | >300 | — | 1.05 | — | — |
| 7 | 0 | 13 | 40 | 185 | — | 2.08 | 3.63 | — |
| 8 | >300 | >300 | >300 | >300 | — | — | — | — |

(*)Consistency Changing Rate = (Consistency at T° C.) − (Consistency at t° C.)/(Consistency at t° C.) wherein t < T.

The above Table shows that the paste-like substances of this invention are slightly inferior to petrolatum, but a reliance on temperature is smaller than that of lanolin and a temperature-stability is higher than that of the esterification product of Patent Kokai No. 54-109917.

Further, a dispersibility of pigment in samples of Table 2 except Sample No. 5 is given in Table 4. The pigment dispersibility was determined by incorporating titanium oxide of 1.0% by weight to a sample warmed to 40° C., stirring together for 15 minutes, transferring the mixture into a scaled test tube and observing a sedimentation velocity of titanium oxide at 40° C.

TABLE 4

| Sample No. | Sedimentation Velocity in Volume % After 0.5 hours | After on hour | After 3 hours |
|---|---|---|---|
| 1 | 4 | 8 | 11 |
| 2 | 7 | 15 | 30 |
| 3 | 10 | 18 | 35 |
| 4 | 87 | 92 | 95 |
| 6 | 75 | 85 | 93 |
| 7 | 5 | 9 | 18 |
| 8 | 30 | 43 | 70 |

As is apparent from the above Table, the paste-like products of this invention are superior in the dispersibility of titanium oxide to petrolatum and lanolin.

Also, the touch tests on Samples of Table 2 are set forth in Table 5 in comparison with the control.

TABLE 5

| Sample No. | Spreading Rate Superior | Equal | Inferior | Stickiness Less | Equal | More | Greasy Touch Less | Equal | More | Flexibility Superior | Equal | Inferior |
|---|---|---|---|---|---|---|---|---|---|---|---|---|
| 1 | 40 | 5 | 5 | 39 | 9 | 2 | 40 | 7 | 3 | 45 | 5 | 0 |
| 2 | 38 | 8 | 4 | 40 | 6 | 4 | 41 | 5 | 4 | 43 | 6 | 1 |
| 3 | 42 | 7 | 1 | 43 | 4 | 3 | 43 | 5 | 2 | 47 | 3 | 0 |
| 5 | 3 | 28 | 19 | 7 | 6 | 37 | 5 | 20 | 25 | 30 | 15 | 5 |
| 6 | 21 | 15 | 14 | 2 | 13 | 35 | 3 | 14 | 33 | 10 | 10 | 30 |
| 7 | 37 | 11 | 2 | 30 | 16 | 4 | 41 | 5 | 4 | 33 | 11 | 6 |
| 8 | 45 | 3 | 2 | 12 | 18 | 20 | 3 | 7 | 40 | 36 | 10 | 4 |

The touch test method was carried out by adding 70 parts by weight of olive oil to 30 parts by weight of a sample to prepare a cream-like substance and testing the touch when the cream is applied to hands on panelers of 50 persons. Control: 30 parts by weight petrolatum and 70 parts by weight olive oil. The above results show that the products of this invention are markedly superior in the touch to petrolatum and lanolin.

Further, a primary irritant effect on the human body was examined by a closed patch test and as a result, none of the products of this invention (Sample Nos. 1–3) exhibited irritant effect on the skin. Thus, they have been found to be useful for a cosmetic material.

The closed patch test: The horniness and sebum on the skin of the upper inner aspect of the arm were removed. The skin surface was covered with a cotton fabric of one inch square on which a sample was applied, and an oiled paper was covered thereon. Further, a paper adhesive plaster was covered in parallel crosses on the oiled paper and furthermore, a bandage was applied thereto. This test was effected on twenty persons of health and rating was conducted after 24 hours, 48 hours and one week, respectively.

Additionally, the above closed patch test was conducted also on the esterification product of 1 mol dipentaerythritol, 4 mols 12-OHst, 1 mol stearic acid, 0.5 mols n-decanoic acid or 2-ethylhexanoic acid and 0.5 mols rhodinic acid, and as a result, no irritant effect was observed.

The products of this invention can be used as a basic material for skin and hair cosmetics, lipsticks and ointments and incorporated in the amount of generally, not more than 80% by weight.

This invention will be illustrated by the non-limitative examples.

EXAMPLE 1

(Synthesis Example of Sample No. 1 of Table 2)

1 mol of diglycerine, 2.1 mols of 12-OHst (purity, more than 90%), 1 mol of rhodinic acid, xylol of 5% by weight based on the total feeds and p-toluenesulfonic acid of 0.2% by weight based on the total feeds were charged into a four-necked flask of 2 l in capacity provided with a stirrer, a thermometer, a nitrogen gas tube and a water separating apparatus equipped with a reflux condenser. Reaction was conducted at 180°–250° C. till a calculated amount of water had been corrected in the water separating apparatus.

After completion of the reaction, the obtained products were subjected to deacidification in conventional methods and then to decolouration with use of a decolouring agent such as an activated clay and active carbon, followed by deodorizing under reduced pressure with steam stripping. Thus, an esterification product consisting mainly of diglycerinemonorhodinic acid 12-OHst ester was obtained.

Acid Value: 0.1, Hydroxyl Value: 150.
Saponification Value: 155, Yield: 75%.

EXAMPLE 2

(Synthesis Example of Sample No. 3 of Table 2)

Reaction of 1.0 mol of dipentaerythritol, 4 mols of 12-OHst, 1.5 mols of stearic acid and 0.5 mols of rhodinic acid was carried out with use of xylol and stannous chloride in the same procedure as in Example 1. After purification an esterification product consisting mainly of dipentaerythritolhemirhodinic acid sesqui stearic acid tetra-12-OHst ester was obtained.

Acid Value: 0.1, Hydroxyl Value: 103.
Saponification Value: 171, Yield: 80%.

EXAMPLE 3

The above esterification products were incorporated into conventional components to prepare various cosmetics. Using products of Examples 1 and 2 and Sample No. 2 of Table 2 as the esterification product, cosmetics of Formulation Nos. 1-7 were prepared, which had good properties and performance.

| Formulation 1 (Lipstick) | |
|---|---|
| Components | Parts by weight |
| Liquid paraffin | 10 |
| Isostearyl alcohol | 8 |
| Cetyl alcohol | 4 |
| Candelilla wax | 10 |
| Ceresin | 15 |
| Bees wax | 10 |
| Esterification product of Ex. 2 | 35 |
| Dyestuffs | 7 |
| Perfumes | 1 |

| Formulation 2 (Cold cream) | |
|---|---|
| Components | Parts by weight |
| Liquid paraffin | 30 |
| Solid paraffin | 5 |
| Esterification product of Sample No. 2 of Table 2 | 20 |
| Stearic acid | 3 |
| Cetyl alcohol | 5 |
| Sorbitan monostearate | 3 |
| Bees wax | 5 |
| Propylene glycol | 4 |
| Preservatives | Small amounts |
| Perfumes | Small amounts |
| Distilled water | 25 |

| Formulation 3 (Ointment) | |
|---|---|
| Components | Parts by weight |
| Esterification product of Ex. 1 | 79 |
| Vitamin E acetate | 1 |
| Liquid paraffin | 10 |
| Petrolatum | 10 |
| Preservatives | Small amount |
| Perfumes | " |

| Formulation 4 (Milky lotion) | |
|---|---|
| Components | Parts by weight |
| Esterification product of Ex. 2 | 50 |
| Polyoxyethylene (20 mols) sorbitan monooleate | 3 |
| Sorbitan monostearate | 2 |
| Preservatives | Small amount |
| Perfumes | " |
| Distilled water | 45 |

| Formulation 5 (Shampoo) | |
|---|---|
| Components | Parts by weight |
| Laurylsulfuric triethanolamine salt | 15 |
| Coconut fatty acid monoethanolamide | 3 |
| Esterification product of Ex. 1 | 2 |
| Preservatives | Small amount |
| Perfumes | " |
| Dyestuffs | Small amount |
| Distilled water | 80 |

| Formulation 6 (Toilet lotion) | |
|---|---|
| Components | Parts by weight |
| Sorbitol | 2 |
| Propylene glycol | 4 |
| Polyoxyethylene (20 mols) oleyl ether | 1 |
| Esterification product of Sample No. 2 of Table 2 | 2 |
| Ethanol | 10 |
| Preservatives | Small amount |
| Perfumes | " |
| Distilled water | 81 |

| Formulation 7 (Hair cream) | |
|---|---|
| Components | Parts by weight |
| Liquid paraffin | 20 |
| Esterification product of Ex. 2 | 25 |
| Stearic acid | 2 |
| Paraffin wax | 3 |
| Polyoxyethylene (20 mols) cetyl ether | 2 |
| Sorbitan monostearate | 1 |
| Propylene glycol | 3 |
| Preservatives | Small amount |
| Perfumes | " |
| Distilled water | 44 |

What is claimed is:

1. An esterification reaction product between a condensate of a polyhydric alcohol having 2-4 hydroxyl groups, represented by the general formula, $$(HO)_nR-O-R(OH)_n$$

wherein R is a polyhydric alcohol of 2-4 hydroxyl groups having removed hydroxyl groups and n is 1, 2, or 3 and an acid mixture comprising 12-hydroxystearic acid and a rosin constituting resin acid whose content is not more than 50 mol % based on the total of 12-hydroxystearic acid and rosin constituting resin acid and does not have more than half the hydroxyl groups of said condensate of the polyhydric alcohol.

2. The esterification product of claim 1 wherein said rosin constituting resin acid is in part substituted by a straight chain fatty acid having 10 or more carbon atoms and/or a branched chain fatty acid having 8 or more carbon atoms.

3. A cosmetic comprising one or more of the esterification reaction products between a condensate of polyhydric alcohol having 2–4 hydroxyl groups, represented by the general formula, (HO)$_n$R—O—R(OH)$_n$ wherein R is a polyhydric alcohol of 2–4 hydroxyl groups having removed hydroxy groups and n is 1, 2, or 3 and an acid mixture comprising 12-hydroxystearic acid and a rosin constituting resin acid whose content is not more, than 50 mol % based on the total of 12-hydroxystearic acid and rosin constituting resin acid and do not have more than half the hydroxyl groups of said condensate of the polyhydric alcohol.

4. A cosmetic comprising one or more of the esterification products of claim 3 wherein said rosin constituting resin acid is in part substituted by a mixture of a rosin constituting resin acid and a straight-chain fatty acid having 10 or more carbon atoms and/or a branched-chain fatty acid having 8 or more carbon atoms.

* * * * *